US00PP08224P

United States Patent [19]

VandenBerg

[11] Patent Number: Plant 8,224

[45] Date of Patent: May 11, 1993

[54] CHRYSANTHEMUM PLANT NAMED LIGHT BRIOSO

[75] Inventor: Cornelis P. VandenBerg, Salinas, Calif.

[73] Assignee: Yoder Brothers, Inc., Barberton, Ohio

[21] Appl. No.: 701,116

[22] Filed: May 16, 1991

[51] Int. Cl.[5] ..... A01H 5/00

[52] U.S. Cl. ..... Plt./74.1

[58] Field of Search ..... Plt./74.1, 82.4

[56] References Cited

U.S. PATENT DOCUMENTS

P.P. 6,497 12/1988 VandenBerg ..... Plt. 74
4,616,099 10/1986 Sparkes ..... 800/1

OTHER PUBLICATIONS

Gosling, ed. 1979, "The Chrysanthemum Manual-6th edition", The National Chrysanthemum Society, London, Essex Telegraph Press, Ltd., pp. 329-336.

Broertjes, et al. 1978, "Application of Mutation Breeding Methods in the Improvement of Vegetatively Propagated Crops", Elsevier Sci. Pub. Co., New York, pp. 162-175.

Broertjes et al. 1980, "A mutant of a mutant of a mutant of a . . . irradiation of progressive radiation-induced mutants in a mutation breeding programme with *Chrysanthemum morifolium*", *Euphytica, 29:526-530.*

Searle et al. 1968, "Chrysanthemums the Year Round", Blanford Press, London, pp. 27-29, 320-327.

Chan, 1966, "Chrysanthemum and rose mutations induced by X-rays", Am. Soc. Hort. Sci. Proc., pp. 613-620.

Broertjes, 1966, "Mutation breeding of chrysanthemums", Euphytica, 15:156-162.

Dowrick et al, 1966, "The induction of mutations in Chrysanthemum using X-and gamma radiation", Euphytica, 15:204-210.

*Primary Examiner*—Howard J. Locker
*Attorney, Agent, or Firm*—Foley & Lardner

[57] ABSTRACT

A Chrysanthemum plant named Light Brioso particularly characterized by its flat capitulum form; daisy capitulum type; light purple ray floret color; diameter across face of capitulum of 108 to 114 mm when fully opened, when grown as a single stem spray cut mum; photoperiodic flowering response to short days of 51 to 66 days; and plant height, with 14 long days after planting rooted cuttings prior to start of short days and with no growth regulator applications, ranges from 109 to 122 cm when grown as a single stem cut mum.

1 Drawing Sheet

The present invention comprises a new and distinct cultivar of Chrysanthemum, botanically known as *Dendranthema grandiflora,* and referred to by the cultivar name Light Brioso.

Light Brioso, identified as 2839 (83-678C09), is a product of a mutation induction program. The new cultivar was discovered and selected by Cornelis P. VandenBerg in March 1987 in a controlled environment in Salinas, Calif., as one flowering plant within a flowering block established as rooted cuttings from stock plants which had been exposed as unrooted cuttings to an X-ray source of 2000 rads in Fort Myers, Fla., in October 1986. The irradiated parent cultivar was the cultivar identified as Brioso, disclosed in U.S. Plant Pat. No. 6,497.

The irradiation program resulting in Light Brioso had as its primary objective the expansion of color ranges of the parent cultivar Brioso. The irradiation program comprised irradiating cuttings of the parent cultivar at irradiation levels of 1500, 1750 and 2000 rads. A total of 593 cuttings harvested from a total of 225 irradiated plants were planted on Feb. 9, Feb. 2 and Jan. 12, 1987, respectively. Of these, 13 initial selections were made, which selections were then revegetated and reflowered. Four consecutive flowerings resulted in discarding 9 of the original 13 selections on Jan. 12, 1988. Three selections were retained as possible introductions, and one selection was retained for possible re-irradiation to obtain a yellow mutation of Brioso, which color was not present in the original selections. The three retained selections will be commercially introduced as Light Brioso, Dark Brioso and Bronze Brioso. The retained selection for possible re-irradiation yielded a spontaneous yellow mutation, which will be commercially introduced as Yellow Brioso. The three mutations in addition to Light Brioso are disclosed in pending plant patent applications of applicant.

The first act of asexual reproduction of Light Brioso was accomplished when vegetative cuttings were taken from the initial selection in May 1987 in a controlled environment in Salinas, Calif., by technicians working under supervision of Cornelis P. VandenBerg.

Horticultural examination of controlled flowerings of successive plantings has shown that the unique combination of characteristics as herein disclosed for Light Brioso are firmly fixed and are retained through successive generations of asexual reproduction.

Light Brioso has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Light Brioso, which, in combination, distinguish this Chrysanthemum as a new and distinct cultivar:

1. Flat capitulum form.
2. Daisy capitulum type.
3. Light purple ray floret color.

4. Diameter across face of capitulum of 108 to 114 mm when fully opened, when grown as a single stem cut mum.

5. Photoperiodic flowerings response to short days of 51 to 66 days.

6. Plant height, with 14 long days after planting rooted cuttings prior to start of short days and with no growth regulator applications, ranges from 109 to 122 cm when grown as a single stem cut mum.

The accompanying photographic drawing is a view of a single stem of Light Brioso, with the colors being as nearly true as possible with illustrations of this type.

Of the commercial cultivars known to the inventor, the most similar in comparison to Light Brioso is the parent cultivar Brioso. All traits of Light Brioso are similar to those of Brioso, except for the ray floret color. The ray floret color of Light Brioso is a significantly lighter purple than the ray floret color of Brioso. The parent cultivar Brioso was never commercially introduced in Colombia, South America, because of low production of flowers per stem, and low night temperature tolerance of the Brioso sports was not evaluated in Colombia. Light Brioso similarly distinguishes from the other Brioso sports by its ray floret color.

In the following description color references are made to The Royal Horticultural Society Colour Chart. The color values were determined on plant material grown as a single stem spray cut mum in Salinas, Calif. on Jun. 20, 1990.

Classification:

*Botanical.*—*Dendranthema grandiflora* cv Light Brioso.

*Commercial.*—Flat daisy spray cut mum.

Inflorescence

A. Capitulum:

*Form.*—Flat.

*Type.*—Daisy.

*Diameter across face.*—108 to 114 mm when fully opened.

B. Corolla of ray florets:

*Color (general tonality from a distance of three meters).*—Light purple.

*Color (upper surface).*—75B, fading to 75D.

*Color (under surface).*—75B to 75C.

Shape.—Oblong

C. Corolla of disc florets:

*Color (mature).*—14A.

*Color (immature).*—144B.

D. Reproductive organs:

*Androecium.*—Present on disc florets only; scant pollen.

*Gynoecium.*—Present on both ray and disc florets.

PLANT

A. General appearance:

*Height.*—109 to 122 cm when grown as a single stem cut mum with 14 long days after planting rooted cuttings prior to start of short days and no growth regulator applications.

B. Foliage:

*Color (upper surface).*—147A.

*Color (under surface).*—147B.

*Shape.*—Lobed and slightly serrated.

I claim:

1. A new and distinct Chrysanthemum plant named Light Brioso, as described and illustrated.

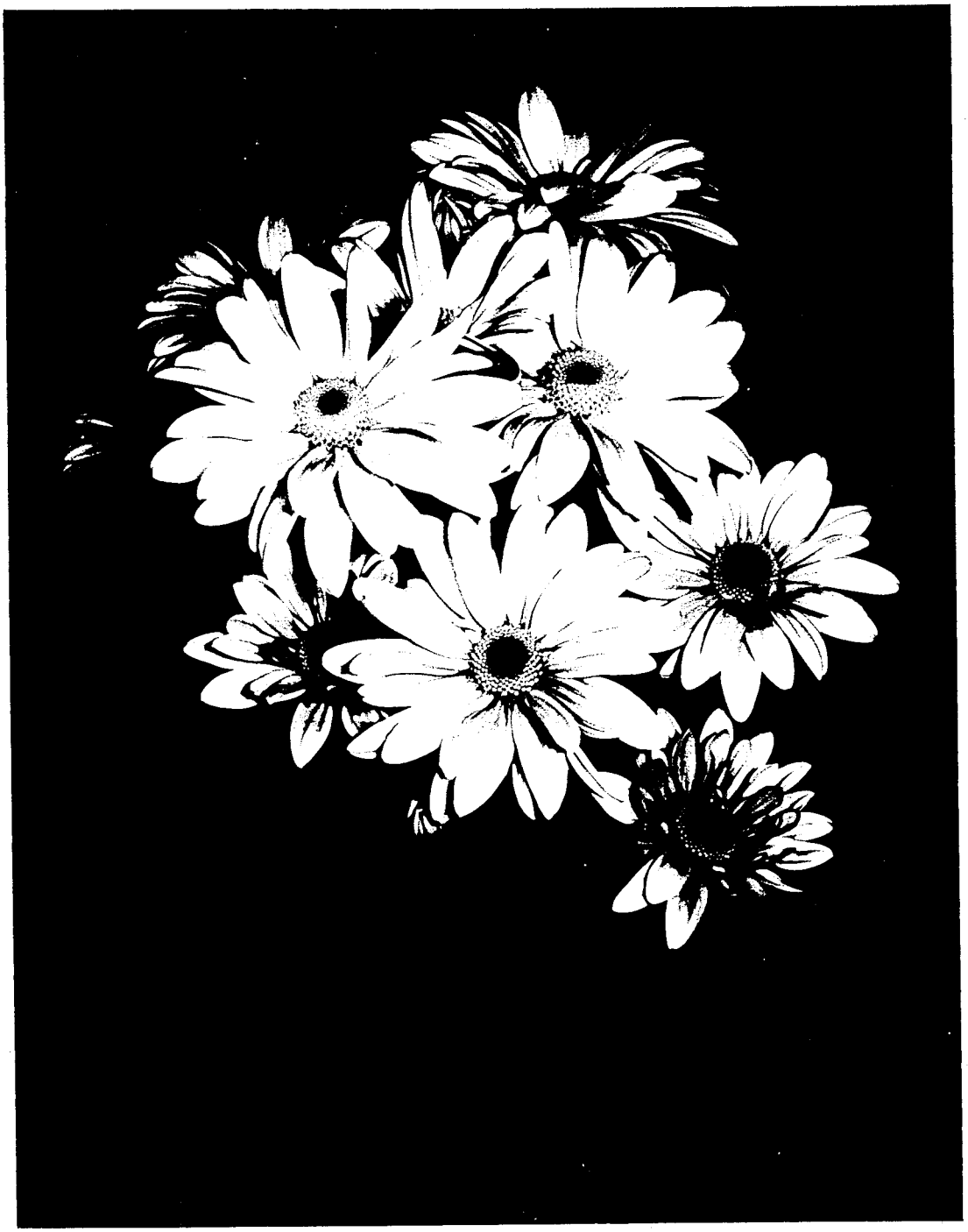

* * * * *